United States Patent

Hoy

[11] Patent Number: 5,542,774
[45] Date of Patent: Aug. 6, 1996

[54] ORTHOTIC JOINT

[76] Inventor: David J. Hoy, 1270 Rosedale Dr., Mansfield, Ohio 44906

[21] Appl. No.: 352,556

[22] Filed: Dec. 8, 1994

[51] Int. Cl.$^6$ .................................................. A61F 5/00
[52] U.S. Cl. ............................ 403/116; 403/73; 403/82; 403/113; 602/16; 602/27
[58] Field of Search ............................. 403/72, 73, 75, 403/82, 113, 116, 117; 602/5, 16, 23, 26, 27

[56]   References Cited

U.S. PATENT DOCUMENTS

| 58,403 | 10/1966 | Goodwin | 602/16 |
|---|---|---|---|
| 206,875 | 8/1878 | Hambrook | 403/116 |
| 3,779,654 | 12/1973 | Horne | 403/62 |
| 3,902,482 | 9/1975 | Taylor | 602/26 X |
| 4,738,252 | 4/1988 | Friddle et al. | 602/16 |
| 4,773,404 | 9/1988 | Townsend | 602/26 X |
| 5,044,360 | 9/1991 | Janke | 403/113 X |
| 5,086,760 | 2/1992 | Neumann et al. | 602/16 X |
| 5,107,824 | 4/1992 | Rogers et al. | 602/26 X |
| 5,302,169 | 4/1994 | Taylor | 602/16 |
| 5,460,599 | 10/1995 | Davis et al. | 602/16 X |

*Primary Examiner*—Blair Johnson
*Assistant Examiner*—Andrea Chop
*Attorney, Agent, or Firm*—Woodling, Krost & Rust

[57]   ABSTRACT

An orthotic joint comprising a first member, a second member and an intermediate plastic member secured together by a pivot. The second member includes a cam follower affixed thereto. The first member and intermediate plastic member include first and second arcuate slots respectively. The first and second arcuate slots are aligned. The first and second members are rotatable with respect to each other. The cam follower protrudes through the second slot and into the first slot. The range of motion is determined by the length of the slot relative to the size of the cam follower.

26 Claims, 7 Drawing Sheets

5,542,774

ORTHOTIC JOINT

FIELD OF THE INVENTION

This invention is an orthotic joint. The present invention is simple, lightweight, and conforms to the human body. The orthotic joint disclosed herein includes a cam follower which determines the range of motion of the second member with respect to the first member. One cam follower may be easily interchanged with a cam follower of a different size. The cam follower may be made of materials which provide a cushioning effect when the second member is moved to a first or second position in the range of motion as will be explained hereinbelow.

RELATED ART

Friddle et al. U.S. Pat. No. 4,738,252 (hereinafter "Friddle") discloses an orthotic joint for use as an ankle, foot and leg support. Friddle does not teach or disclose cam followers which are interchangeable with each other without disassembly of the entire joint. Nor does Friddle teach or disclose cam followers made from shock absorbent materials.

The present invention employs first and second members which have first and second joining portions which each have concave and convex surfaces. An intermediate plastic member of the present invention has intermediate concave and convex surfaces. Some of the surfaces of the joining portions of the first and second members interfit with the surfaces of the intermediate plastic member. The second member of the invention rotates relative to the first member around a pivot means comprised of a screw and a nut.

OBJECTS OF THE INVENTION

It is an object of the present invention to provide an orthotic joint which is lightweight. The preferred embodiment of the present invention includes first and second members made from aluminum. Typically, a person in need of an orthotic device requires one of lightweight and high strength.

It is a further object of the present invention to provide an orthotic joint which includes a cam follower which is easily interchanged with other cam followers having different sizes. The interchangeability is accomplished by removing a single screw which secures the cam follower to the second member and then simply substituting another cam follower in its place. A first arcuate slot is located in the first member. The cam follower resides partially in the first arcuate slot.

It is a further object of the present invention to provide an orthotic joint which employs a cam follower made of a shock absorbing material. This permits relative rotational movement of the second member with respect to the first member, or vice versa, between limiting first and second positions. This shock absorbing or cushioning effect enables use of the orthotic device in a more comfortable and therapeutic manner.

It is a further object of the present invention to provide an orthotic joint which interfits with the human body. The preferred embodiment of the present invention is an orthotic joint for interconnecting a foot and leg brace about the ankle of the user.

It is a further object of the present invention to provide an orthotic joint which includes an intermediate plastic member which enables the first and second members to rotate relative to each other with relatively low friction. The intermediate plastic member further includes a second arcuate slot which is of the same size as the first arcuate slot of the first member.

BRIEF DESCRIPTION OF THE DRAWINGS

FIG. 1 illustrates the second member 12 in a first position with respect to the first member 10.

FIG. 3' is a side sectional view of the first member 10. FIG. 3' illustrates, among other things, the first transitional portion 42 and the first connecting portion 41.

FIG. 4' illustrates a side sectional view of the second member 12. FIG. 4' illustrates the second transitional portion 52 and the second connecting portion 51.

FIG. 5' illustrates a top view of the cam and the screw for affixing the cam follower to the second member.

FIG. 6' illustrates a side sectional view of the intermediate plastic member.

FIG. 7 is a top plan view similar to the view shown in FIG. 1 except that a different cam follower member is shown. In particular, the cam follower member is spaced equally about the screw affixing the cam follower to the second member.

FIG. 8 illustrates the second member 12 in a second position with respect to the first member 10.

DETAILED DESCRIPTION OF THE INVENTION

Figure 1:
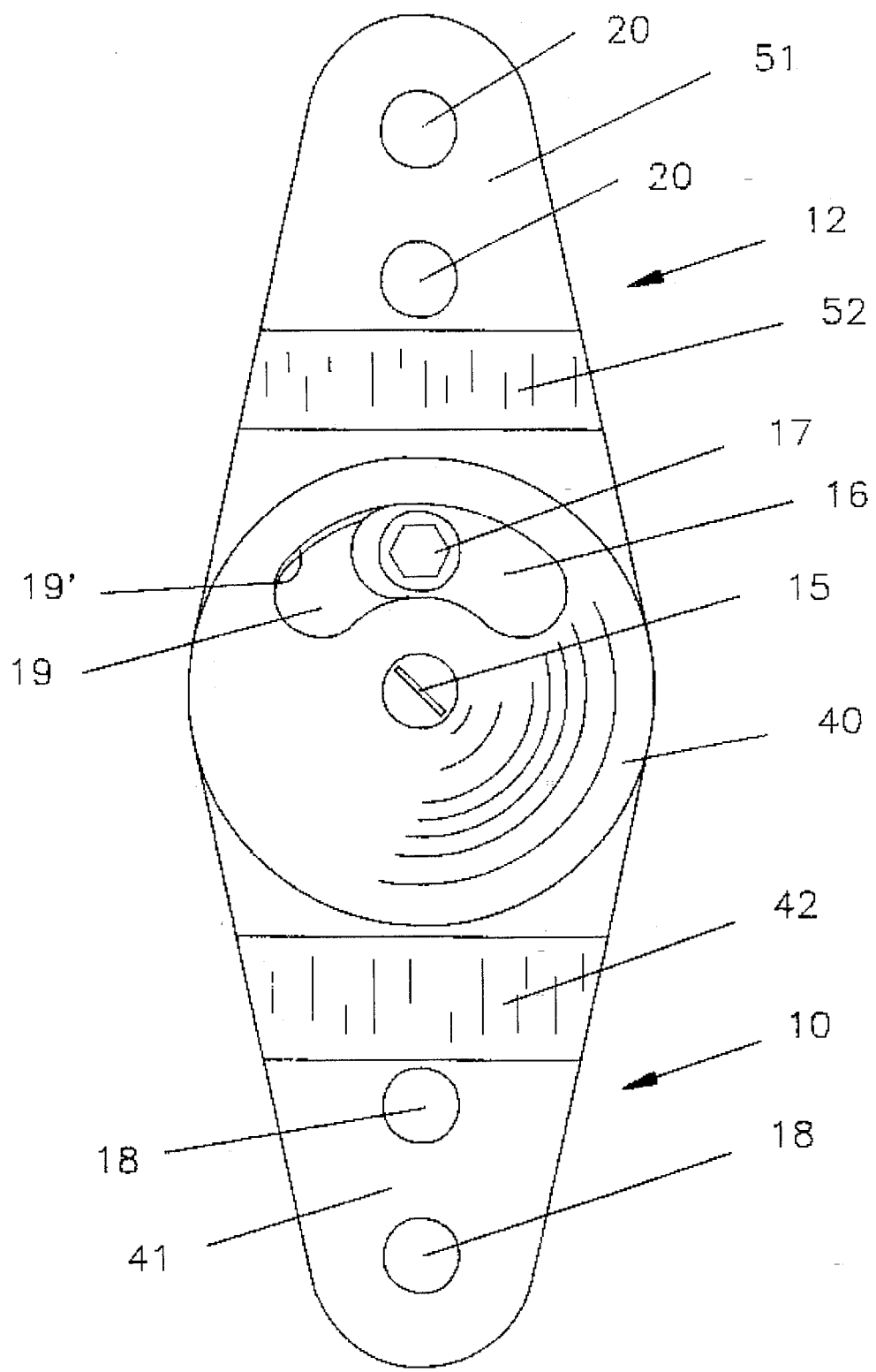
FIG. 1 is a top plan view of the invention illustrating the first member 10 and the second member 12 assembled together.
Figure 2:
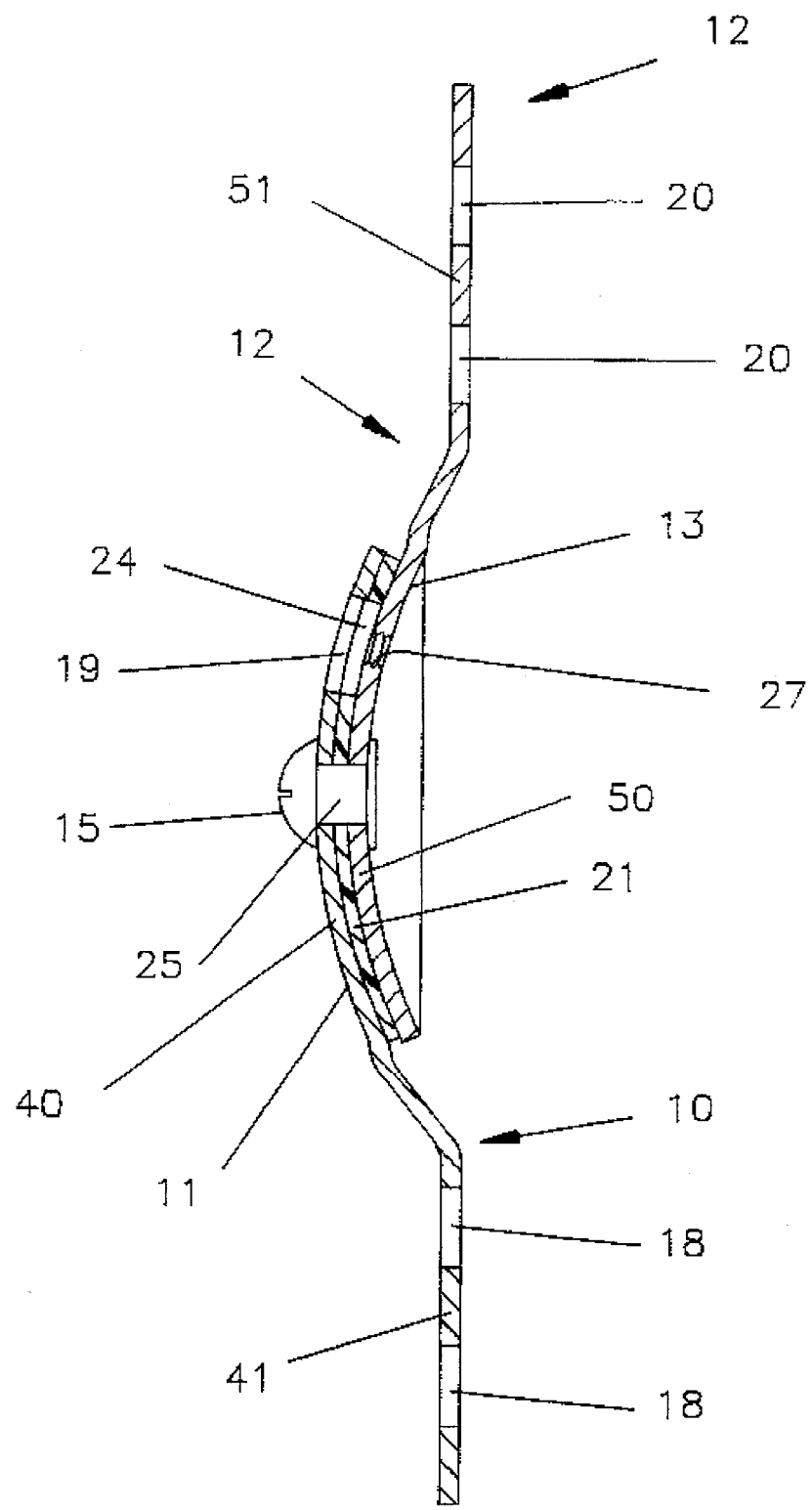
FIG. 2 is a side sectional view of the invention illustrating the first member 10, the second member 12, the intermediate plastic member 21, the pivot screw 15 and nut 25.

FIGS. 1 and 2 illustrate the invention assembled. First member 10 and second member 12 are shown in FIGS. 1 and 2. FIG. 1 is a top plan view of the invention illustrating openings 18 for connection of the first member 10 to a foot brace (not shown). FIG. 1 illustrates openings 20 for connection of the second member 12 to a leg brace (not shown). FIG. 1 prominently illustrates the cam follower member 16 and screw 17. The second member 12 is in a first position as illustrated in FIG. 1.

First member 10 includes a first connecting portion 41, a first transitional portion 42 and a first joining portion 40. See FIGS. 3 and 3'. Second member 12 includes a second connecting portion 51, a second transitional portion 52 and a second joining portion 50. See FIGS. 4 and 4'. FIG. 2 illustrates the invention assembled without the cam follower member 16 and screw 17.

It can be seen from FIG. 1 that differently sized cam follower members permit a different range of motion. Additionally, slot 19 and first wall means 19' are shown in FIG.

1. It can be seen from FIG. 1 that a longer slot 19 permits a different range of motion. From FIG. 1 it can be seen that if the first member 10 is fixed or held in place then second member 12 may be rotated with respect thereto in a counterclockwise direction. However, as shown in FIG. 1, the second member may not be rotated clockwise relative to fixed member 10. If a differently sized cam follower is used, for example a smaller one (in length) or one which is oriented equally about the threaded opening 27 (FIG. 7), the second member may be rotated in a clockwise direction relative to fixed first member 10.

Figure 3:
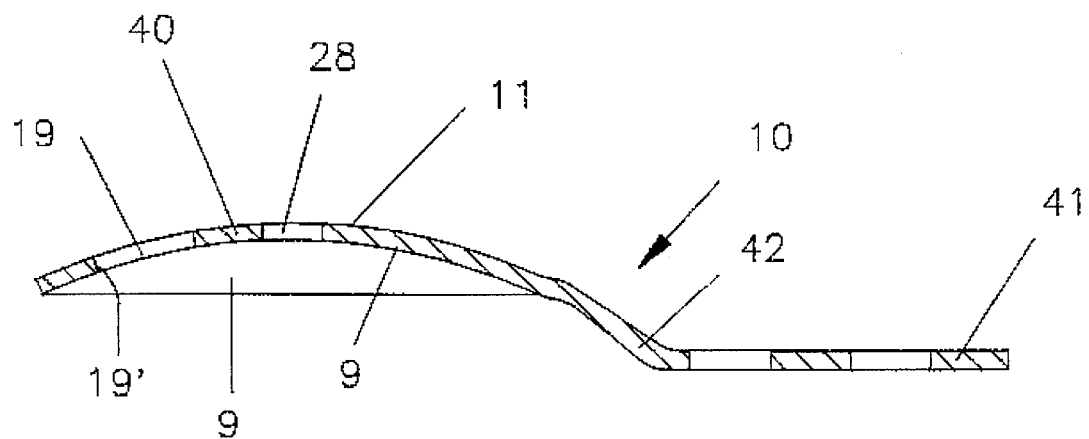
FIG. 3 is a top plan view of the first member 10 illustrating the first connecting portion 41, the first transitional portion 42 and the first joining portion 40. Also illustrated in FIG. 3 is the first arcuate slot 19.
Figure 3:
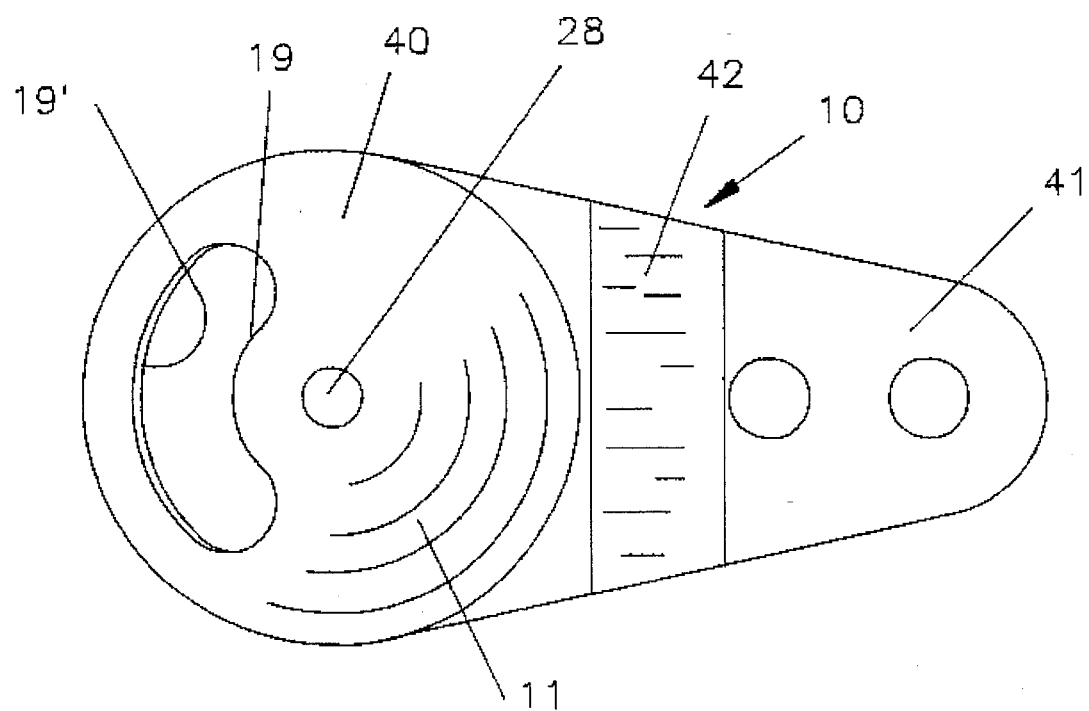

FIGS. 3 and 3' illustrate the first member 10. In particular, the first concave surface 9, the first convex surface 11 and the first arcuate slot 19 of the first member are shown in FIG. 3'. By concave it is meant that the surface curves inwardly. By convex it is meant that the surface curves outwardly. FIG. 3 illustrates the first cylindrical bore 28 in the joining portion 40 of the first member. The joining portion 40 of the first member 10 has a first concave surface 9 and a first convex surface 11.

The intermediate plastic member 21 has an intermediate convex surface 23, an intermediate concave surface 22 and a second arcuate slot 24. See FIGS. 6 and 6'. The second member 12 includes a joining portion 50 having a second concave surface 13 and a second convex surface 14. See FIGS. 4 and 4'. A cam follower 16 is affixed to the second member 12 by a threaded screw 17. The threaded screw 17 passes through bore 30 of the cam follower 16 and affixes the cam follower 16 to the second member 12 by means of threaded opening 27.

Figure 4:
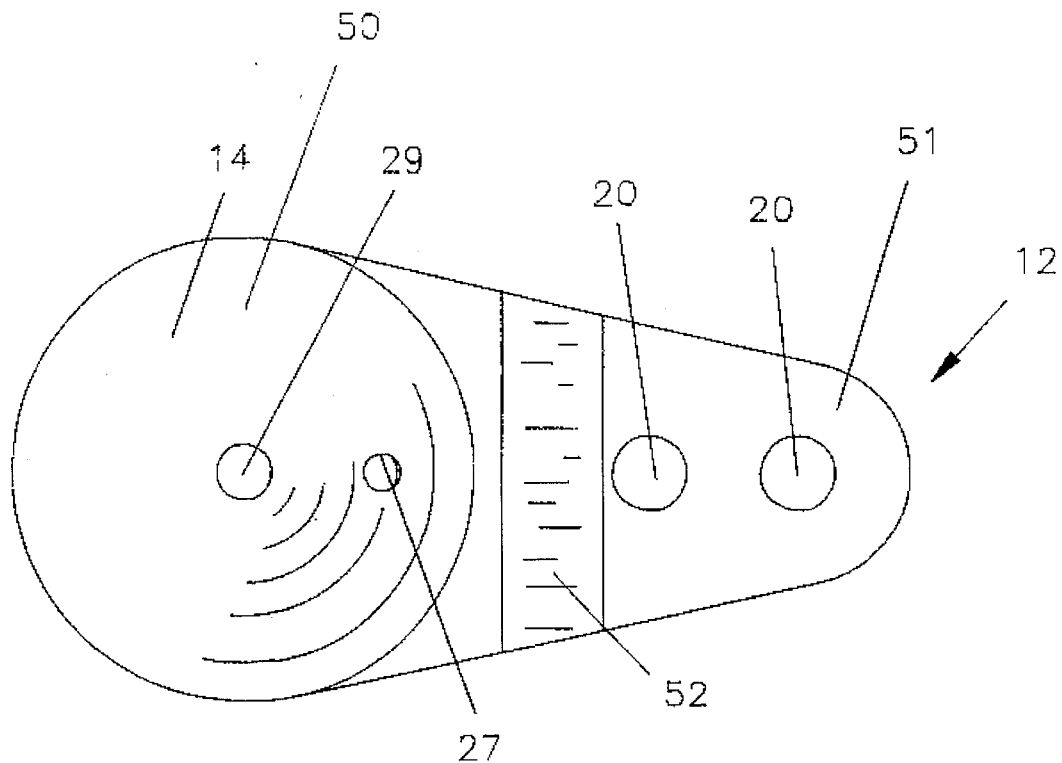
FIG. 4 illustrates a top plan view of the second member 12.
Figure 4:
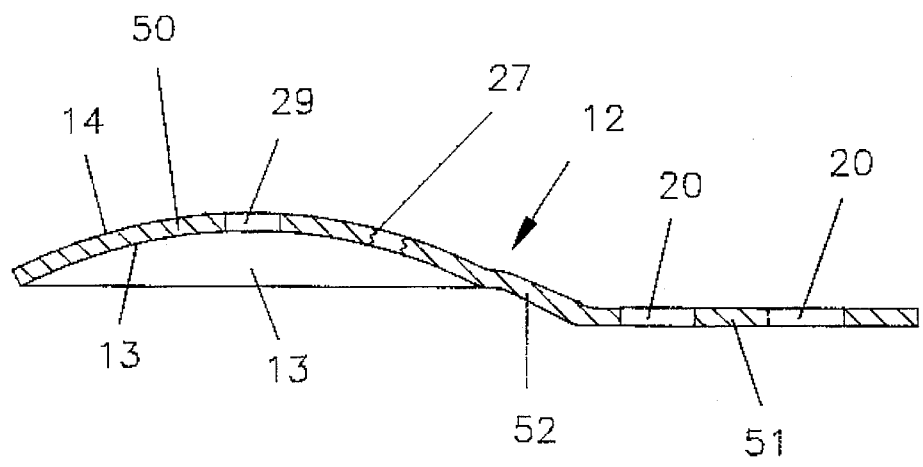

The first member, the intermediate plastic member, and the second member are secured together by screw 15 and nut 25. See FIG. 2. The second convex surface 14 of the second member 12 interfits with the intermediate concave surface 22 of the intermediate plastic member 21. FIGS. 4 and 4' illustrate the second member 12. The intermediate convex surface 23 of the intermediate plastic member interfits with the first concave surface 9 of the first member 10.

The second arcuate slot 24 of the intermediate plastic member 21 is aligned with the first arcuate slot 19 of the first member. The cam follower member 16 protrudes through said second arcuate slot 24 of said intermediate plastic member and into said first arcuate slot 19 of said first member. The first joining portion of the first member has a first cylindrical bore 28 therein. The intermediate plastic member has a third cylindrical bore 26 therein. The second joining portion of the second member has a second cylindrical bore 29 therein. The first member 10, second member 12 and intermediate member 21 are secured together by screw 15 and nut 25 which generally reside in the first, third and second cylindrical bores.

The intermediate plastic member 21 permits low friction movement of the second member 12 with respect to the first member 10. See, FIG. 2. The intermediate plastic member serves as a bearing for the second member to rotate relative to the first member. It will be apparent to those skilled in the art that the intermediate plastic member may be eliminated from the invention without departing from the spirit and scope of this invention.

First wall means 19' form a first arcuate slot 19 in the first member 10. See, FIG. 3. The first arcuate slot 19 may have different lengths depending on the range of motion desired. From FIGS. 2 and 3' it is seen that the joining portion 40 of the first member 10 is distally spaced from the first connecting portion 41 of the first member. The first connecting portion 41 of the first member 10 resides generally in a plane. The transitional portion 42 of the first member connects the first connecting portion and the joining portion 40 together.

Figure 5:
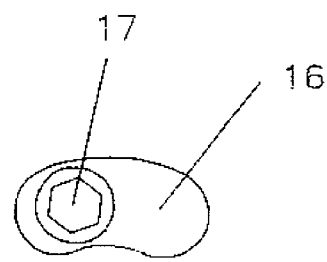
FIG. 5 illustrates a side sectional view of the cam member 16 and the bore 30 therethrough.
Figure 6:
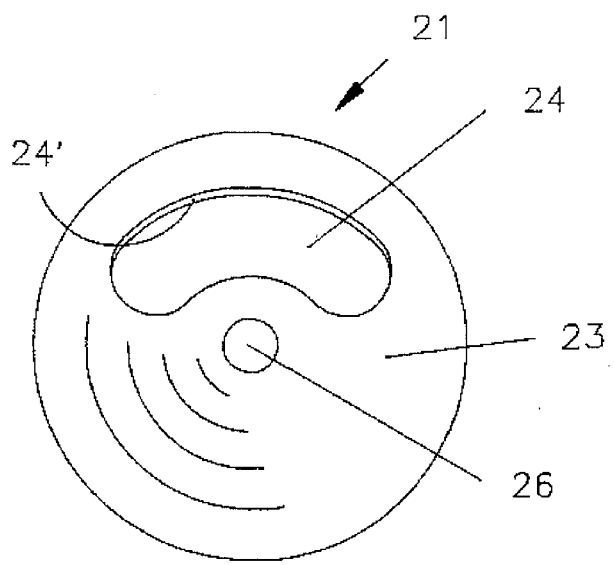
Figure 5:
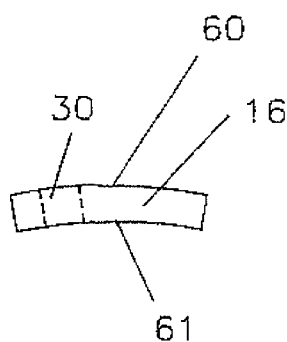

The preferred embodiment of the invention includes a cam follower 16 having a cam follower convex surface 60 and a cam follower concave surface 61. See FIGS. 5 and 5'. The cam follower concave surface 61 interfits with the second convex surface 14 of the second joining portion 50 of the second member 12. See, FIG. 4'. However, it will be apparent to those skilled in the art that the cam follower need not necessarily include a cam follower concave surface which interfits with the second convex surface of the second joining portion of the second member.

Differently shaped cam followers are contemplated. For instance, one such cam follower 16' may be shaped such that it resides bilaterally with respect to the threaded opening 27 in the second member. See FIG. 7. FIG. 1 illustrates a cam follower which occupies more space in the clockwise direction of the arcuate slot 19 with respect to the threaded opening 27. As previously stated, this prevents rotation of the second member 12 in the clockwise direction with respect to the first member 10. FIG. 1 illustrates the second member 12 in the first position with respect to first member 10. FIG. 8 illustrates the second member 12 in the second position with respect to first member 10. Second member 12 is rotatable with respect to member 10 between first (FIG. 1) and second (FIG. 8) positions. The present invention provides an orthotic joint which selectively provides many different ranges of motion by simply substituting different cam followers.

Figure 7:
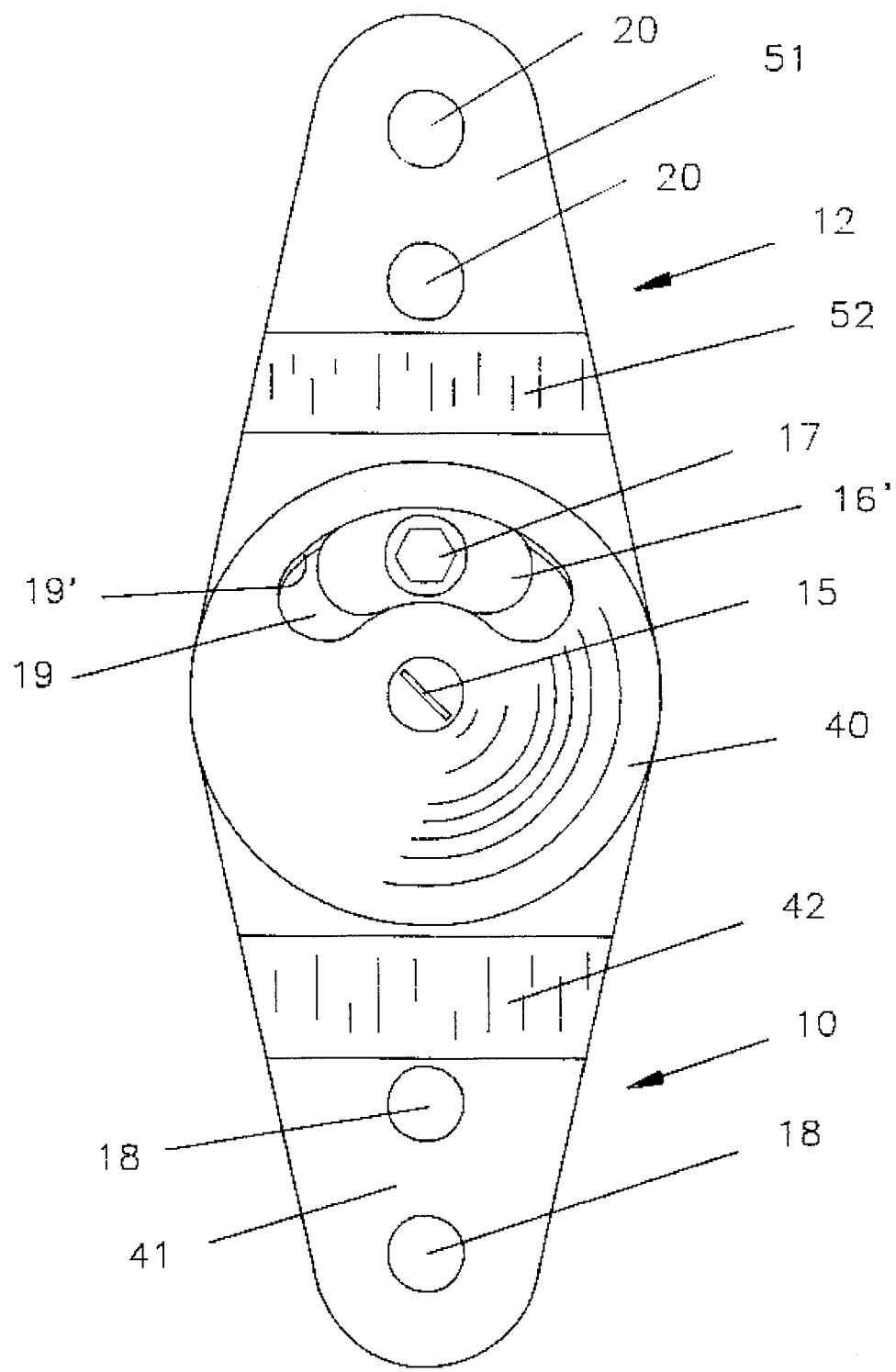
FIG. 7 illustrates another embodiment of the invention.
Figure 8:
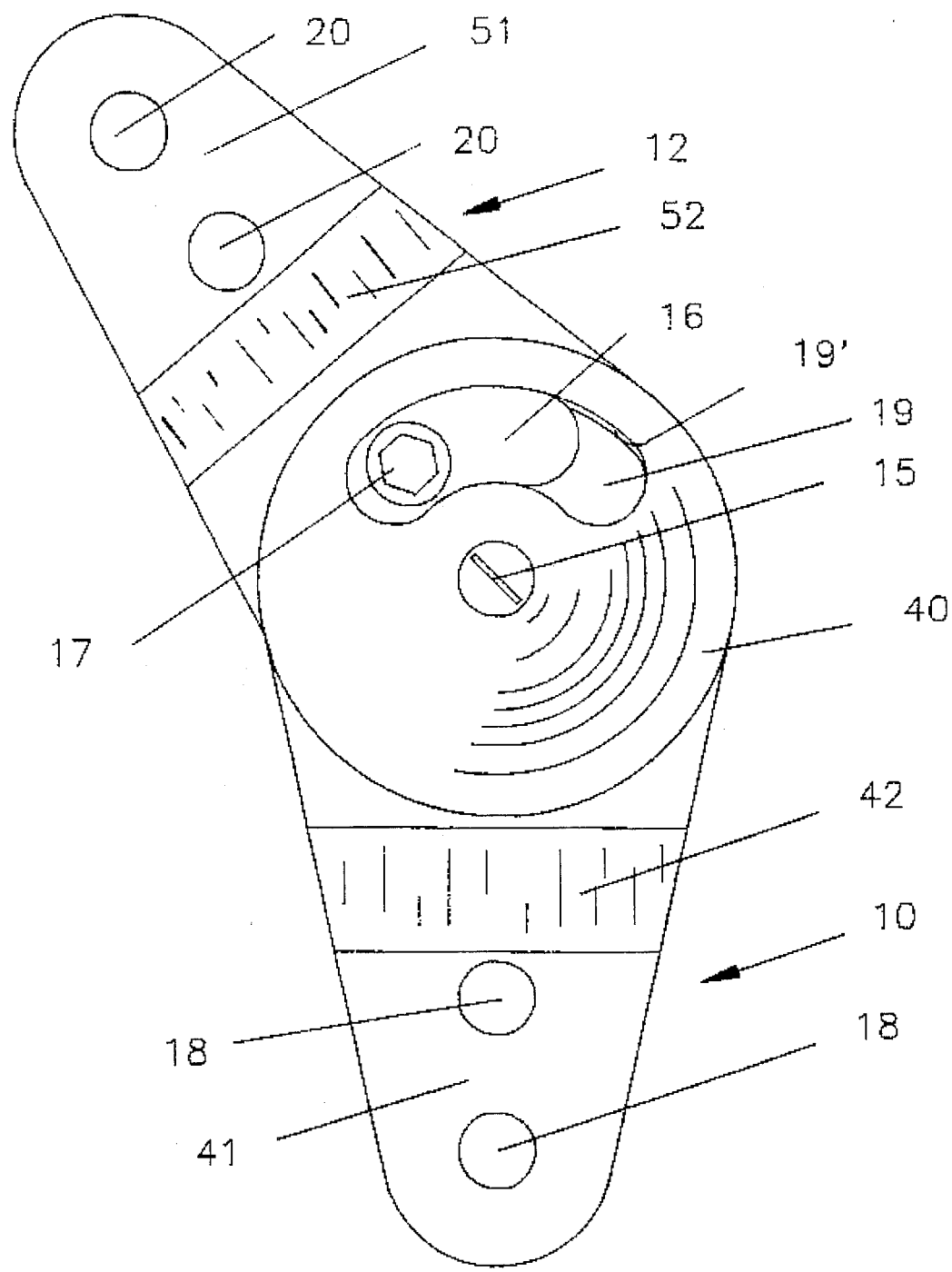
FIG. 8 is a top plan view of the invention illustrating the first member 10 and the second member 12 assembled together similar to FIG. 1.

FIG. 7 illustrates another embodiment of the invention. In particular, FIG. 7 illustrates another cam follower member 16' which permits rotation of the second member 12 with respect to the first member 10 in both the clockwise and counterclockwise directions.

Figure 6:
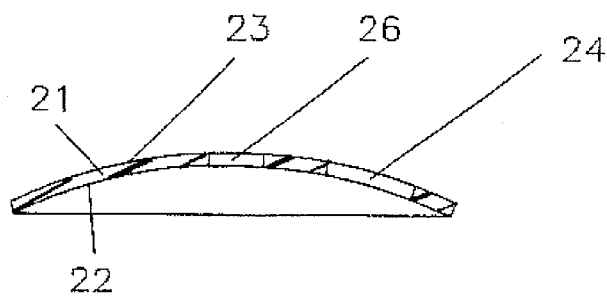
FIG. 6 illustrates a top view of the intermediate plastic member 21 including the second arcuate slot 24.

FIG. 6 illustrates the intermediate plastic member 21. FIG. 6' illustrates the intermediate concave surface 22 and the intermediate convex surface 23. FIG. 6 and 6' also illustrate the second arcuate slot 24 and the second wall means 24' which form the second arcuate slot 24. The third cylindrical bore 26 is also illustrated in FIGS. 6 and 6'. It will be observed from FIG. 2 that the first connecting portion 41 of the first member and the second connecting portion 51 of the second member reside generally in the same plane. Referring to FIG. 2, it will be observed that the first and second joining portions 40, 50 are located distally with respect to the first and second connecting portions. The distal location of the joining portions provides space for a user's body to occupy if necessary. For instance, when the preferred embodiment of the present invention, FIGS. 1–6 and 8, is used with a foot and leg support, space is provided for the ankle of the user. Openings 18 allow connection to a foot support (not shown) and openings 20 allow connection to a leg support (not shown). Attachment means other than openings 18, 20 are contemplated for connection to a first and second orthotic body supports.

The orthotic joint of the present invention may be used for joints other than the ankle, foot and leg. Different materials may be used for the cam follower 16. Rubber, polyurethane, or a silicone elastomer may be employed as materials of the cam follower. These materials are generally known as viscoelastic materials. These materials absorb the shock that may occur when the second member is rotated from the first position (FIG. 1) to the second position (FIG. 8) or vice versa. The preferred embodiment employs cam followers made of metal. The preferred embodiment employs first and second members made of aluminum. Many different materials may be used instead of aluminum for the first and second members. For instance, plastic may be used. Aluminum is used because it is lightweight.

The invention has been described in detail with particular emphasis on the preferred embodiments thereof, but it should be understood that variations and modifications within the spirit and scope of the invention may occur to those skilled in the art to which the invention pertains.

What is claimed is:

1. An orthotic joint comprising a first member, a second member, a pivot means, a plurality of interchangeable cam followers, one of said plurality of interchangeable cam followers removably mounted to said second member, a first slot in said first member, said one of said interchangeable cam followers protruding into said first slot, said second member rotatable with respect to said first member between a first position and a second position about said pivot means, and, said first and said second positions being adjustable by interchanging said one of said interchangeable cam followers with another of said interchangeable cam followers.

2. An orthotic joint as claimed in claim 1 wherein said plurality of interchangeable cam followers are made of polyurethane.

3. An orthotic joint as claimed in claim 1 wherein said plurality of interchangeable cam followers are made of a silicone elastomer.

4. An orthotic joint as claimed in claim 1 wherein said plurality of interchangeable cam followers are follower is made of rubber.

5. An orthotic joint as claimed in claim 1 wherein said plurality of interchangeable cam followers are made of a viscoelastic material.

6. An orthotic joint as claimed in claim 1 wherein said first slot is an arcuately shaped slot.

7. An orthotic joint as claimed in claim 6 further including an intermediate plastic member residing between said first member and said second member.

8. An orthotic joint as claimed in claim 7 wherein said pivot means includes a threaded screw and a nut.

9. An orthotic joint as claimed in claim 8 wherein said first member includes a first joining portion and said second member includes a second joining portion, said first joining portion of said first member includes a first concave surface and first convex surface, said second joining portion of said second member includes a second concave surface and a second convex surface, said intermediate plastic member includes an intermediate concave surface and an intermediate convex surface, said intermediate plastic member includes a second arcuate slot, said one of said interchangeable followers protruding into said first arcuate slot of said first member and said second arcuate slot of said intermediate plastic member, said second convex surface of said second member interfitting said intermediate concave surface of said intermediate plastic member, said intermediate convex surface of said intermediate plastic member interfitting said first concave surface of said first member, and said pivot means secures said first member, said intermediate plastic member, and said second member together.

10. An orthotic joint as claimed in claim 9 wherein said first member further includes a first connecting portion and a first transitional portion and wherein said second member further includes a second connecting portion and a second transitional portion, said first transitional portion connecting said first connecting portion and said first joining portion, and said second transitional portion connecting said second connecting portion and said second joining portion.

11. An orthotic joint as claimed in claim 10 wherein said first connecting portion resides substantially in a plane and said second connecting portion resides substantially in said plane, and wherein said first joining portion is distally spaced from said first connecting portion by said first transitional portion and wherein said second joining portion is distally spaced from said second connecting portion by said second transitional portion.

12. An orthotic joint as claimed in claim 11 wherein said first connecting portion of said first member includes a first attachment means for connecting to a first orthotic support and said second connecting portion of said second member includes a second attachment means for connecting to a second orthotic support.

13. An orthotic joint as claimed in claim 12 wherein said first attachment means comprises a first cylindrical opening and said second attachment means comprises a second cylindrical opening.

14. An orthotic joint as claimed in claim 13 wherein said first attachment means comprises a plurality of first cylindrical openings and said second attachment means comprises a plurality of second cylindrical openings.

15. An orthotic joint as claimed in claim 14 wherein said first and said second members are made of aluminum.

16. An orthotic joint comprising a first member, a second member, an intermediate plastic member, a pivot means, and a plurality of interchangeable cam followers, said second member includes a respective one of said interchangeable cam followers removably mounted thereto, said first member includes a first arcuate slot, said intermediate plastic member includes a second arcuate slot, said intermediate plastic member residing between said first and said second member, said second arcuate slot of said intermediate plastic member being aligned with said first arcuate slot of said first member, said respective one of said interchangeable cam followers protruding into said first and said second arcuate slots, and said second member is rotatable with respect to said first member between a first position and a second position about said pivot means, and said first and second positions being adjustable by interchanging said respective one of said interchangeable cam followers with another of said plurality of interchangeable cam followers.

17. An orthotic joint as claimed in claim 16 wherein said respective one of said interchangeable cam followers is movable between a first and a second position within said first and said second arcuate slots.

18. An orthotic joint as claimed in claim 17 wherein said pivot means includes a threaded screw and a nut, said pivot means secures said first member, said intermediate plastic member and said second member together.

19. An orthotic joint as claimed in claim 18 wherein said plurality of interchangeable cam followers are made of polyurethane.

20. An orthotic joint as claimed in claim 18 wherein said plurality of interchangeable cam followers are made of a silicone elastomer.

21. An orthotic joint as claimed in claim 18 wherein said plurality of interchangeable cam followers are made of rubber.

22. An orthotic joint comprising a first member, a second member, an intermediate plastic member, a pivot means, and a plurality of interchangeable cam followers, said first member includes a first connecting portion, a first transitional portion, and a first joining portion, said first joining portion of said first member includes a first wall means forming a first arcuate slot therein, said first joining portion of said first member includes a first convex surface, a first concave surface, and a first cylindrical bore, said first connecting portion of said first member residing generally in a plane, said first joining portion of said first member residing distally from said first connecting portion, said first transitional portion connecting said first joining portion and said first connecting portion together, said second member includes a second connecting portion, a second transitional portion, and a second joining portion, said second joining portion of said second member includes a second convex surface and a second concave surface, a respective one of said cam followers includes a cam follower convex surface, a cam follower concave surface and a cam follower bore, said second joining portion of said second member includes a threaded opening therein, a cam follower screw, said cam follower screw residing in said cam follower bore and engaging said threaded opening of said second member affixing said respective one of said cam followers to said second member, said second convex surface of said second member interfitting said cam follower concave surface, said second joining portion of said second member includes a second cylindrical bore, said second connecting portion of said second member residing generally in a plane, said second joining portion of said second member residing distally from said second connecting portion, said second transitional portion connecting said second joining portion and said second connecting portion together, said intermediate plastic member includes second wall means forming a second arcuate slot, said intermediate plastic member includes an intermediate convex surface, an intermediate concave surface, and a third cylindrical bore, said intermediate plastic member resides between said first joining portion of said first member and said second joining portion of said second member, said pivot means extending through said first cylindrical bore of said first member, said third cylindrical bore of said intermediate plastic member, and said second cylindrical bore of said second member, said first arcuate slot of said first member being aligned with said second arcuate slot of said intermediate member, said respective one of said cam followers residing in said first and second arcuate slots, said second convex surface of said second member interfitting with said intermediate concave surface of said intermediate plastic member and said intermediate convex surface of said intermediate plastic member interfitting with said first concave surface of said first member, and said second member being rotatable with respect to said first member between a first position and a second position about said pivot means, and said first and said second positions being adjustable by interchanging said respective one of said cam followers with another of said plurality of interchangeable cam followers.

23. An orthotic joint as claimed in claim 22 wherein said plurality of interchangeable cam followers are made of polyurethane.

24. An orthotic joint as claimed in claim 22 wherein said plurality of interchangeable cam followers are made of a silicone elastomer.

25. An orthotic joint as claimed in claim 22 wherein said plurality of interchangeable cam followers are made of a viscoelastic material.

26. An orthotic joint as claimed in claim 22 wherein said first connecting portion of said first member includes a first attachment means for connecting to a first orthotic support and said second connecting portion of said second member includes a second attachment means for connecting to a second orthotic support.

* * * * *